US009272092B2

(12) United States Patent
Aguerre et al.

(10) Patent No.: US 9,272,092 B2
(45) Date of Patent: Mar. 1, 2016

(54) MACHINE AND METHOD FOR THE AUTOMATIC PREPARATION OF INTRAVENOUS MEDICATION

(71) Applicant: KIRO ROBOTICS, S.L., Arrasate (ES)

(72) Inventors: Jean-Philippe Aguerre, Itxassou (FR); Borja Lizari Illarramendi, Vitoria-Gasteiz (ES); Susana Soto Iglesias, Arrasate-Mondragón (ES); Naiara Telleria Garay, Arrasate-Mondragón (ES); Gerardo Cajaraville Ordoñana, Donostia (ES); Maria José Tamés Alonso, Donostia (ES)

(73) Assignee: KIRO ROBOTICS, S.L., Arrasate-Mondragon (ES)

( * ) Notice: Subject to any disclaimer, the term of this patent is extended or adjusted under 35 U.S.C. 154(b) by 156 days.

(21) Appl. No.: 14/226,774

(22) Filed: Mar. 26, 2014

(65) Prior Publication Data
US 2014/0202588 A1    Jul. 24, 2014

Related U.S. Application Data

(63) Continuation of application No. 13/276,119, filed on Oct. 18, 2011, now Pat. No. 8,820,365.

(30) Foreign Application Priority Data

Jun. 17, 2011    (EP) .................................... 11382202

(51) Int. Cl.
*A61M 5/178* (2006.01)
*B65B 3/00* (2006.01)
*B65B 3/04* (2006.01)

(52) U.S. Cl.
CPC .............. *A61M 5/1782* (2013.01); *B65B 3/003* (2013.01); *B65B 3/04* (2013.01)

(58) Field of Classification Search
CPC ........ A61M 5/1782; B65B 3/003; B65B 3/04
USPC ........ 141/2, 27, 192, 329, 330; 700/218, 245; 422/81
See application file for complete search history.

(56) References Cited

U.S. PATENT DOCUMENTS 2,702,505 A    2/1955    Nelson
4,842,028 A    6/1989    Kaufman
(Continued)

FOREIGN PATENT DOCUMENTS

CN    201195165    2/2009
CN    201195165 Y    2/2009
(Continued)

OTHER PUBLICATIONS

European Extended Search Report on European Patent Application No. 11382203.5; Dec. 8, 2011; 7 Pages; European Patent Office, Rijswijk, Netherlands.
(Continued)

*Primary Examiner* — Timothy L Maust
(74) *Attorney, Agent, or Firm* — Edell, Shapiro & Finnan, LLC

(57) ABSTRACT

A machine for the automatic preparation of an intravenous medication is provided. In one implementation the machine has a chamber with a starting products area where at least one receptacle is disposed with a base product from which the intravenous medication is generated, a transfer tools area where at least one transfer tool that is used to prepare the required medication is disposed, a prepared products area where at least one container to house the prepared medication is disposed, and a first robot to handle the transfer tool, the first robot being adapted to transport the transfer tool between the transfer tools area, the starting products area and the prepared products area in order to prepare the intravenous medication.

19 Claims, 5 Drawing Sheets

(56) References Cited

U.S. PATENT DOCUMENTS

| | | | |
|---|---|---|---|
| 5,309,959 A * | 5/1994 | Shaw | B65B 3/003 |
| | | | 141/103 |
| 5,341,854 A * | 8/1994 | Zezulka | A61J 1/20 |
| | | | 141/1 |
| 5,431,201 A * | 7/1995 | Torchia | A61J 1/20 |
| | | | 141/100 |
| 5,443,791 A | 8/1995 | Cathcart et al. | |
| 5,479,969 A * | 1/1996 | Hardie | B65B 3/003 |
| | | | 141/103 |
| 5,555,920 A | 9/1996 | Godolphin | |
| 7,128,105 B2 * | 10/2006 | Tribble | A61J 1/20 |
| | | | 141/198 |
| 7,186,378 B2 | 3/2007 | Dunfee et al. | |
| 7,783,383 B2 * | 8/2010 | Eliuk | A61J 1/20 |
| | | | 141/1 |
| 7,848,848 B2 | 12/2010 | Busacca et al. | |
| 7,931,859 B2 * | 4/2011 | Mlodzinski | A61J 1/20 |
| | | | 221/123 |
| 8,201,592 B2 | 6/2012 | Van Vreeland et al. | |
| 8,267,129 B2 | 9/2012 | Doherty et al. | |
| 8,386,070 B2 * | 2/2013 | Eliuk | A61J 1/20 |
| | | | 141/1 |
| 8,820,365 B2 * | 9/2014 | Aguerre | B65B 3/003 |
| | | | 141/192 |
| 8,857,476 B2 * | 10/2014 | Koike | A61J 3/002 |
| | | | 141/114 |
| 2008/0199353 A1 | 8/2008 | Mlodzinski et al. | |
| 2010/0268167 A1 | 10/2010 | Mattioli et al. | |

FOREIGN PATENT DOCUMENTS

| | | |
|---|---|---|
| EP | 1759776 A1 | 3/2007 |
| GB | 2259081 A | 3/1993 |
| WO | 9515142 | 6/1995 |
| WO | 2008047390 A1 | 4/2008 |
| WO | 2011007341 A1 | 1/2011 |

OTHER PUBLICATIONS

European Partial Search Report on European Patent Application No. 11382202.7-2308; Nov. 24, 2011; 5 Pages; European Patent Office, Munich, Germany.

* cited by examiner

MACHINE AND METHOD FOR THE AUTOMATIC PREPARATION OF INTRAVENOUS MEDICATION

CROSS-REFERENCE TO RELATED APPLICATIONS

This application is a continuation of U.S. application Ser. No. 13/276,119, filed Oct. 18, 2011, which relates to and claims the benefit and priority to European Patent Application EP11382202, filed Jun. 17, 2011.

TECHNICAL FIELD

This invention relates to machines for the automatic preparation of intravenous medication.

BACKGROUND

Machines for the automatic preparation of intravenous medication are known. The medication is the result of the mixture of specific amounts of different base products, and in many cases, once the medication has been prepared, it is packaged in containers adapted to house it. The base products are stored in vials and a preset amount is removed from them, sufficient to generate the required intravenous medication.

In many hospitals, for instance, medications are prepared manually, though an increasing number of hospitals now have a machine to prepare medications. The vials or receptacles housing the necessary base products are disposed in the machine, and the machine handles the vials in order to create a mixture of the base products they house, in the required quantities for each of them and in the required order.

One of these machines is disclosed in document WO 2009147252 A1. The machine comprises different work areas that are separate to each other, such as a storage area where the receptacles or vials are disposed, and a preparation area where the final medication, based on the base products present in the vials, is prepared.

SUMMARY OF THE DISCLOSURE

According to one implementation a machine is provided that comprises a starting products area where the base products from which the required medication is generated are disposed, a transfer tools area where at least one syringe that is used to prepare the required medication is disposed, a prepared products area to house the prepared medication, and at least one robot to communicate the different areas with each other.

The robot, the starting products area, the transfer tools area, and the prepared products area are disposed in the same cabinet or chamber of the machine, so that the robot is adapted to communicate the areas with each other in the chamber, transporting the receptacles, the syringe and/or the container from one area to another to prepare the required medication.

As a result, as all the operations for the preparation of the intravenous medication can be carried out in the same cabinet or chamber, the different areas are not isolated from each other and, for example, in the event of the machine breaking down a user can access the chamber and carry out the preparation of the medication manually, being able to make use of the space occupied by the machine for the same medication preparation function even when the machine is not working. In addition, as it does not comprises storage members and/or carrousels where different receptacles and containers are stored, for example, there is no need to use additional movement tools to position the required receptacles and containers in a final position adapted for the preparation of the intravenous medication in progress as they are already disposed in the final position.

These and other advantages and characteristics of the invention will be made evident in the light of the drawings and the detailed description thereof.

BRIEF DESCRIPTION OF THE DRAWINGS

FIG. 2b is a perspective view of the chamber or cabinet of FIG. 2a.

DETAILED DESCRIPTION

Figure 1:
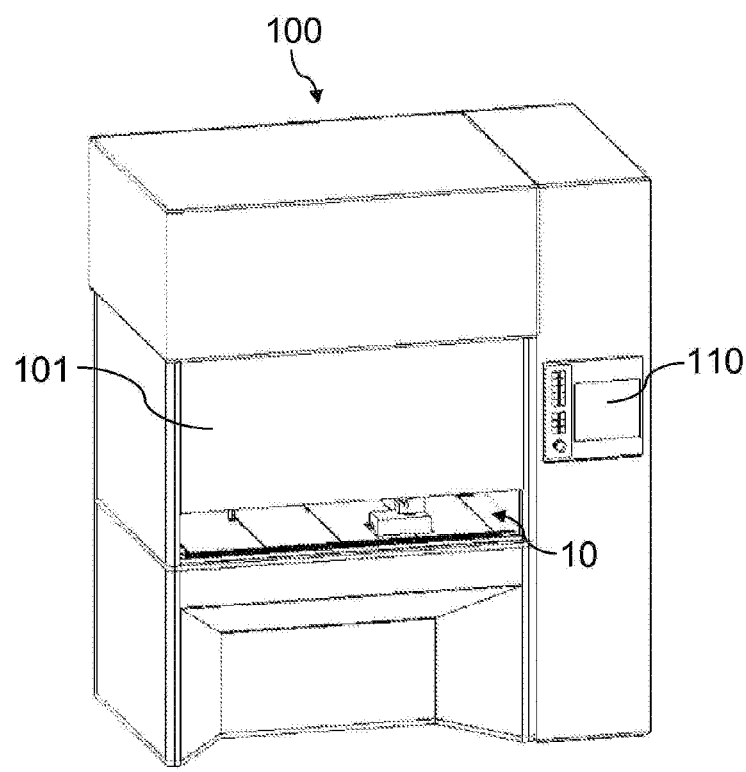
FIG. 1 shows a perspective view of an embodiment of the machine of the invention.

FIG. 1 shows an embodiment of a machine 100 designed for the preparation of medication from at least one base product, in particular for the preparation of intravenous cytotoxic medicines.

Figure 2A:
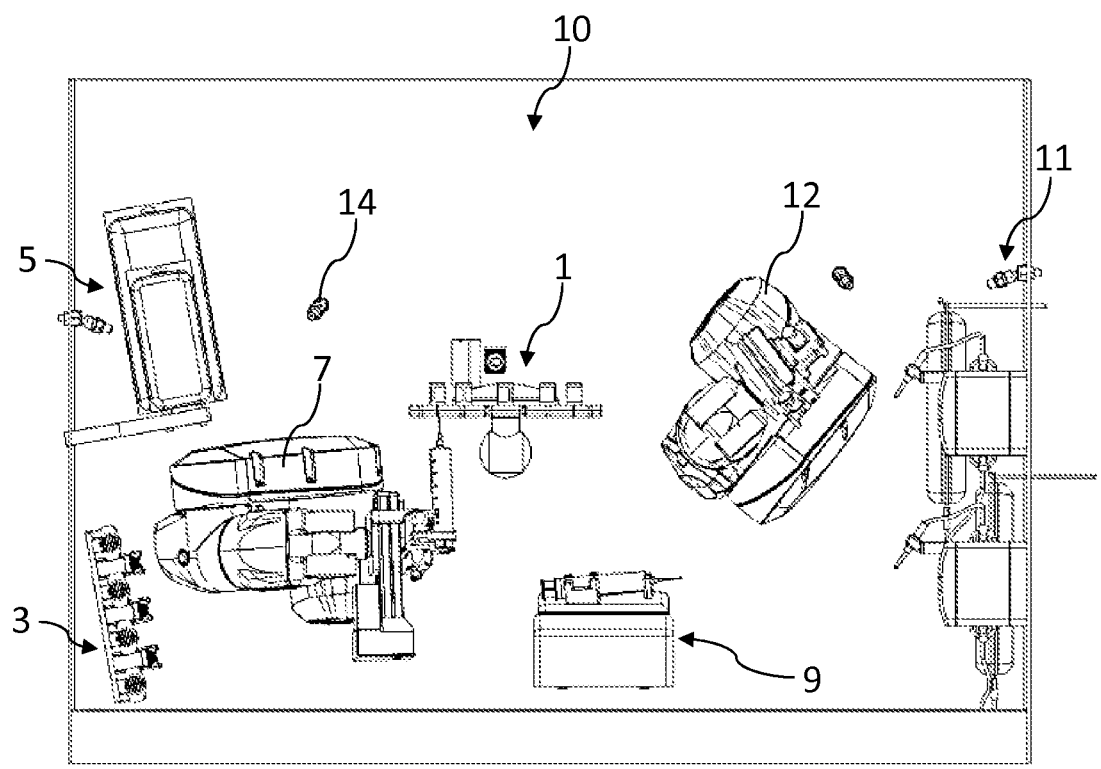
FIG. 2a shows a front view of a chamber or cabinet of the machine of FIG. 1, where the automatic preparation of medication is carried out.
Figure 2B:
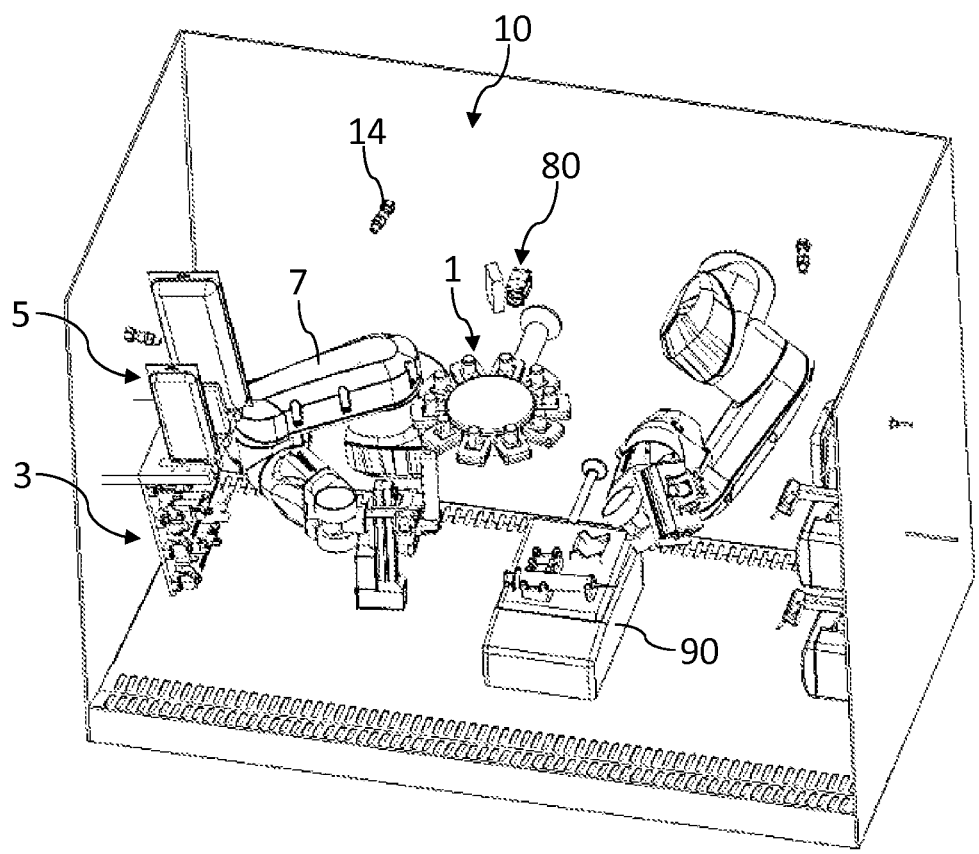
Figure 3:
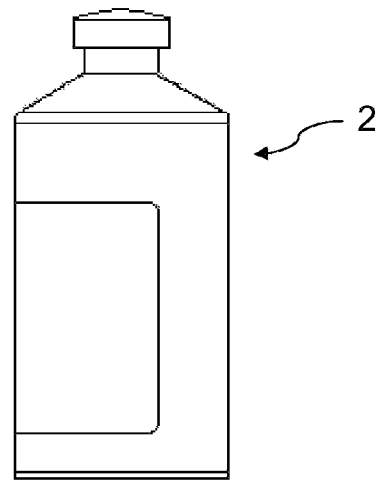
FIG. 3 shows an example of a receptacle among those used in the machine of FIG. 1.
Figure 4:
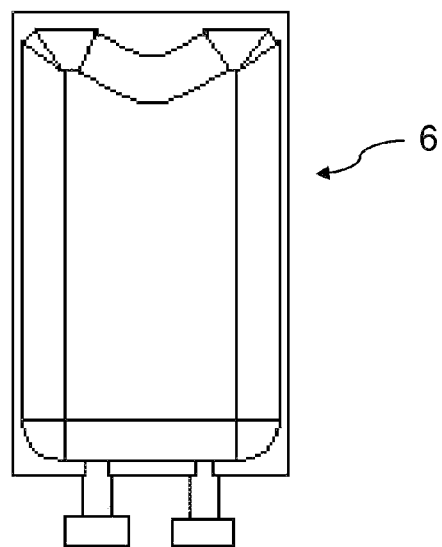
FIG. 4 shows an example of a container among those used in the machine of FIG. 1.

With reference to FIGS. 2a and 2b, a cabinet or chamber 10 of the machine 100 is shown. In one implementation the machine 100 comprises a starting products area 1 where base products are disposed and from which the required medication is generated. The base products are preferably housed inside receptacles 2 that may correspond with vials such as the one shown by way of example in FIG. 3. Disposed within a transfer tools area 3 of the machine 100 are as many transfer tools 4 as will be needed during the preparation of the medication. A transfer tool 4 may be, for example, a syringe. Disposed in a prepared products area 5 is at least one container 6 adapted to house the prepared medication. The container 6 may be a perfusion bag such as the one shown by way of example in FIG. 4. The container may also comprise a bottle, an elastomeric infuser or other type of container. Also disposed within the chamber 10 is at least one robot 7 that is adapted to transport and/or handle the receptacles 2, the transfer tool 4, and/or the container 6 to carry out the preparation. In one implementation the at least one robot 7 comprises an articulated arm, The robot 7 and the areas 1, 3 and 5 are disposed in the same cabinet or chamber 10 of the machine 100, so that the robot 7 is disposed to communicate the areas 1, 3 and 5 with each other in the chamber 10 transporting the receptacles 2, the transfer tool 4 and/or the container 6 from one area to another to prepare the required medication.

In one embodiment, the robot 7 is adapted to transport a transfer tool 4 from one area to another to prepare the required medication, without transporting the receptacles 2 and the containers 6, so that the robot 7 carries the transfer tools 4 to the corresponding receptacles 2 and containers 6. The robot 7 is thus adapted to pick up a transfer tool 4 from the transfer tools area 3 and transport it to the starting products area 1 to cause the total or partial filling of the transfer tool 4 with the necessary or required amount of the base product present in a corresponding receptacle 2, and to then transport the transfer tool 4 to the prepared products area 5 to cause the transfer tool 4 to totally or partially empty into at least one corresponding container 6. Although the medication is normally generated with a single base product, in some cases a mixture of different base products is needed to obtain the required medication, cases in which a different transfer tool 4 is used for each base product. Once the contents of a transfer tool 4 have been discharged in a container 6, the robot 7 deposits the transfer tool 4 in the transfer tools area 1 and picks up a new transfer tool 4 disposed beforehand in the transfer tools area 1 in order to fill it totally or partially with a new base product, the aforementioned process starting again until the required amount of the base product is deposited in the container 6. In the container 6 is thus generated the mixture of base products used to create the required medication, the pre-prepared medication being deposited or stored in the container 6.

Figure 5:
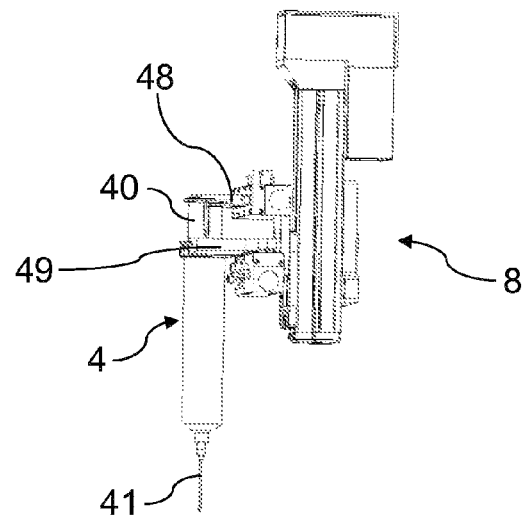
FIG. 5 shows a tool for a robot of the machine of FIG. 1, which is adapted to pick up and handle transfer tools, with a transfer tool.

In one embodiment the machine 100 comprises a tool 8 that is fixed to the robot 7, shown in FIG. 5, by means of which the robot 7 holds and handles the transfer tools 4. In one implementation the tool 8 comprises claws 49 or equivalent members controlled by the robot 7 to hold a transfer tool 4, which can be a syringe, and comprises an actuator 48 to act on a plunger 40 of the syringe and enable the total or partial filling and/or emptying of the syringe, the movement of the plunger 40 being controlled by the robot 7, which is controlled by control means such as a microprocessor for example (not shown in the figures), of the machine 100. The receptacles 2 may be disposed in a substantially vertical position with the inlet access disposed in the bottom part, and the robot 7 positions the syringe 4, by means of the tool 8, in a substantially vertical position facing the corresponding receptacle 2 in order to fill, totally or partially, the syringe with the corresponding base product. The same occurs in order to empty the contents of the syringe in the container 6. Once the syringe has been positioned in this way, the robot 7 causes a vertical upwards movement of the syringe towards the corresponding receptacle 2 or container 6 until a needle 41 (or an equivalent element that may be used as an injection system) of the syringe is introduced into the receptacle 2 or the container 6, and the actuator 48 then acts on the plunger 40 of the syringe in order to fill the syringe with the required amount of the base product present in the corresponding receptacle 2 or in order to empty the contents of the syringe into the corresponding container 6. Evidently, the plunger 40 moves in an opposite direction when filling and emptying a syringe.

In one embodiment the machine 100 can also comprise, in the chamber 10, a reconstituting area 11 to reconstitute the receptacles 2 comprising a powdered or lyophilised base product in their interior. Reconstituting should be understood as making a powdered or lyophilised base product soluble in liquid or dissolving it, and in the reconstituting area 11 the machine 100 comprises dosage means (not shown in the figures), which can be conventional, and whose function is to introduce a specific liquid into the receptacle 2 with the base product to be reconstituted. For the reconstitution, the machine 100 can comprise a second robot 12 that is adapted to pick up a receptacle 2 from the starting products area 1 in order to transport it to the reconstituting area 11, and to transport it again to the starting product tool area 1 once the contents of the receptacle 2 have been reconstituted, so that a transfer tool 4 can now be filled with the contents of the receptacle 2. In one embodiment the machine 100 also comprises a tool or tools (not shown in the figures) that are disposed in the starting products area 1 and support the receptacles 2. In such an embodiment the second robot 12 may pick up the corresponding tool in order to transport the required receptacle 12. Although in the embodiment of FIG. 2a the machine comprises a second robot 12 for the reconstitution, it is also possible to use the robot 7 to perform the function without the need to include a second robot 12.

In one embodiment the machine 100 also comprises a weighing area 9 located in the chamber 10 that includes one or more scales 90 (or other weighing apparatus) used to weigh both the transfer tools 4 and the receptacles 2. The corresponding robot 7 or 12 disposes a transfer tool 4 or a receptacle 2 on the scales 90 in order to weigh it.

Figure 6:
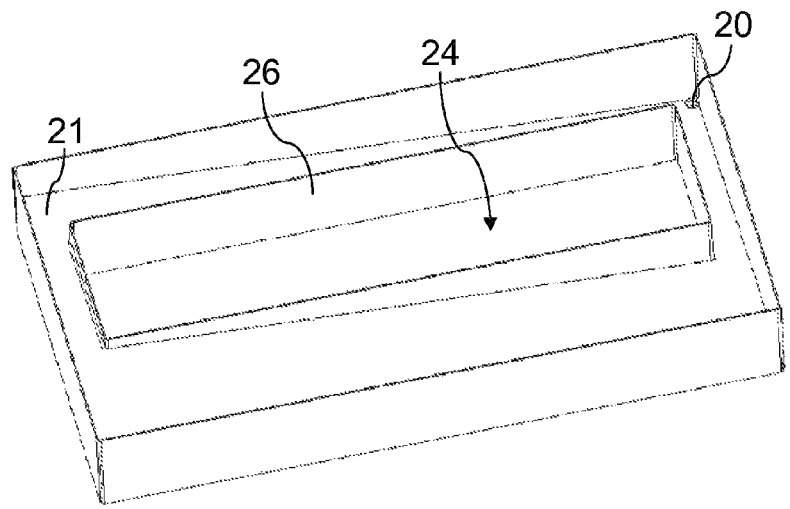
FIG. 6 shows drainage means of the machine of FIG. 1.

The machine 100 can also comprise cleaning means or system to clean the chamber 10 automatically once the medication has been prepared or after various preparation cycles. The cleaning means comprise at least one hole 14 through which a sprayed liquid or a fluid in the form of a jet is introduced into one or more certain areas of the chamber 10 or in the chamber 10 in its entirety, which can be water. As a result, the fluid sweeps the surfaces of the chamber 10 clean and also washes away any dirt that that may have adhered to the robot 7, to the second robot 12, and/or the different areas 1, 3, 5, 9 and 11, for example, which are made, at least in the outer part, of a material resistant to the fluid to be used (for example water). The machine 100 may also comprise drainage means as shown in FIG. 6, to drain the chamber 10 of the fluid introduced by the cleaning means. The drainage means may comprise at least one drainage hole 20 disposed in the bottom part of the chamber 10 and at least one drainage surface 21 in the bottom part of the chamber 10, on which at least part of the fluid introduced falls. The drainage surface 21 comprises a slope that runs downwards to the drainage hole 20 to direct the fluid towards the drainage hole.

The machine 100 may also comprise drying means or system to dry cleaning fluid from the walls that delimit the chamber 10 and to dry the elements within the chamber 10. In one implementation the drying means comprises a chamber inlet access (not shown in the figures) that may be situated in a top part of the chamber 10, and at least one airflow router (not shown in the figures), such as a fan, that forces airflow into the chamber 10 through the chamber inlet access. In one implementation an outlet access 24 is provided in the bottom of the chamber 10 that accommodates the removal of moisture from the chamber as airflow is being forced through the chamber by means of the airflow router. As a result, thanks to the drainage and to the drying the fluid is removed from the chamber 10 completely, resulting in the suitable cleaning of the chamber 10. The inlet and outlet accesses and the airflow system can also be used during the preparation of the required medication, to ensure that the air in the chamber 10 is purified and insulated from the exterior and also that potentially contaminated air does not escape from the chamber 10 to the exterior (protection of the user and the environment). In one embodiment, the machine 100 also comprises a filter not shown in the figures which is disposed in the outlet access 24, so that the air that is removed from the chamber 10 passes through the filter where toxic or unwanted particles are prevented from escaping from the chamber 10. In one implementation the filter is disposed and laid flat within the outlet access and is surrounded by drainage surfaces 21 of the drainage means, and each one of the drainage surfaces 21 comprises a wall 26 on the side closest to the filter, thereby ensuring that during the preparation or the drainage no liquid reaching the drainage surfaces 21 can dampen the filter. (I do not understand this.) Evidently the filter can be disposed in another position in which it does not need to be surrounded by drainage surfaces 21, such as against an internal wall of the chamber 10. The filter may be an activated carbon filter.

The machine 100 may also comprise a user interface 110 that allows a user to program the functionality of the robot 7 or the robots 7 and 12 so that they act in the manner required to obtain the medication.

A method for the preparation of intravenous medication according to one implementation is explained below. Firstly, the receptacles 2 with the required base products from which the required medication is generated are manually disposed in the starting products area 1, the transfer tools 4 necessary to prepare the medication are manually disposed in the transfer tools area 3, and the necessary containers 6 are manually disposed in the prepared products area 5. For this purpose, the user or users carrying out these operations accesses the chamber 10 by partially or completely opening a cover 101 of the machine 100 that covers the front of the chamber 10, so that it is also kept insulated from the exterior.

Before or after these manual operations have been carried out, a user enters the necessary data or information into a control system of the machine 100 through the interface 110. Once the components have been properly placed in the chamber 10 and the control system has been properly programmed, the user after entering any necessary data into the control system may act upon the control system to cause the procedure to start. The necessary data may be, for example, information related to the base products to be used and to the amounts of each base product to be used. Alternatively, this information may also be pre-stored in a memory of the machine, for example (entered when carrying out a pre-preparation or even entered before any preparation is carried out), in which case the user only has to indicate which preparation should be carried out.

Once the necessary receptacles 2, transfer tools 4 and container 6 have been disposed in their corresponding areas 1, 3 and 5, the robot 7 carries out a preparation operation in which it picks up a transfer tool 4 from the transfer tools area 3, transports the transfer tool 4 to the starting products area 1, causes the transfer tool 4 to be partially or completely filled with a specific amount of a base product present in a corresponding receptacle 2, transports the transfer tool 4 with the base product to the prepared products area 5, and partially or completely empties the transfer tool 4 into a corresponding container 6. The robot 7 carries out as many preparation operations as are necessary to prepare the required amount of medication and may use a different transfer tool 4 for each of the different base products. When all the necessary operations have been completed, when the required medication is deemed to have been prepared, the machine 100 can indicate the end of the preparation with visual and/or sound alarms, for example. Once the required medication has been prepared, a user may access the chamber 10 to collect the container 6 housing the medication. Similarly, once the robot 7 has used a transfer tool 4 the robot 7 may dispose of the transfer tool 4, depositing it, for example, in a location designed for such a purpose and not shown in the figures.

In one implementation the robot 7 only handles the transfer tools 4 and fills them with a liquid base product. In such a case, in one implementation the control means is adapted to identify if any receptacles 2 comprise a powdered or lyophilised base product, and if this is the case, a second robot 12 controlled by the control means transports the receptacle 2 from the starting products area 1 to a reconstituting area 11 where the base product is dissolved, changing to a liquid state, and returns it once more to the starting products area 1. In one implementation the second robot 12, after the corresponding liquid has been introduced into the receptacle 2 in the reconstituting area 11, shakes the receptacle 2 so that the base product dissolves correctly before transporting it to the starting products area 1. The reconstituting operation can be performed at the same time as the preparation operation performed by the robot 7, while one robot prepares the mixture with base products in a liquid state (the robot 7), the other robot (second robot 12) can at the same time be reconstituting a receptacle 2 whose contents are not in a liquid state. This results in a very flexible and speedy preparation method. As stated above, in another embodiment the reconstituting operation can also be carried out by the robot 7, without the need for the machine 100 to comprise a second robot 12.

The method may also comprise a weighing phase to determine whether the amount of a base product contained in a syringe is suitable or not. For this purpose the robot 7 transports an empty transfer tool 4 originating from the transfer tools area 3 to the weighing area 9 where it is weighed, and does the same with the transfer tool 4 containing the base product recently acquired from a receptacle 2. The control means compares both weight measurements and if the amount is correct, the robot 7 transports the transfer tool 4 to the prepared products area 5. If the amount is not correct two circumstances can arise. If the amount of base product in the transfer tool is smaller than that required, the transfer tool 4 is taken to the starting products area 1 so that it can be filled with more of the corresponding base product. If, on the other hand, the amount of base product in the transfer tool is greater than that required, the excess amount is deposited in a receptacle (not shown in the figures) located in the chamber 10 and set up for this purpose or is disposed in a specific area of the chamber 10. In both cases the weighing is carried out again until the required amount is obtained.

The method can also comprise a weighing phase for the reconstituted receptacle, in which the second robot 12 transports the reconstituted receptacle 2 to the weighing area 9 to weigh it. It can thus be ascertained if the amount of liquid added to the receptacle for the reconstitution is correct.

To ensure that the base product to be filled in a transfer tool 4 is the correct one, the machine 100 can comprise at least one video system, such as a video camera 80, for example, and the receptacles 2 can comprise an adhesive label identifying the base product it houses and the state in which it houses it. Thus, by reading the label it can be determined if a receptacle 2 is housing the required base product or not, and if it is in a liquid state or not.

What is claimed is:

1. A machine for the automatic preparation of an intravenous medication, the machine comprising a chamber having a starting products area where at least one receptacle is disposed with a base product from which the intravenous medication is generated, a transfer tools area where at least one transfer tool that is used to prepare the required medication is disposed, a prepared products area where at least one container to house the prepared medication is disposed and where the transfer tool is used to place the base product into the container, and a first robot to handle the transfer tool, the first robot adapted to transport the transfer tool between the transfer tools area, the starting products area and the prepared products area in order to prepare the intravenous medication, wherein the chamber further comprises a reconstituting area adapted to receive the at least one receptacle for the purpose of dissolving powdered or lyophilised contents that may be contained in the at least one receptacle, the first robot adapted to pick up the receptacle from the starting products area, transport the receptacle to the reconstituting area where the contents of the receptacle are dissolved, and transport the receptacle back to the starting products area.

2. A machine according to claim 1 wherein the first robot is adapted to transport the container within the chamber.

3. A machine according to claim 1, further comprising a tool that is fixed to the first robot and which is adapted to hold and manipulate the transfer tool.

4. A machine according to claim 1, wherein each of the receptacles in the starting products area is supported by a handling tool, each of the receptacles having a different handling tool, the first robot being adapted to pick up each of the handling tools to transport the receptacles to the reconstituting area.

5. A machine according to claim 1, further comprising a cleaning system to clean at least part of the chamber, the cleaning system comprising at least one hole situated within a wall of the chamber through which a sprayed liquid or a fluid in the form of a jet is introduced into one or more of the starting products area, the prepared products area and transfer tools area of the chamber.

6. A machine according to claim 5, further comprising drainage system adapted to evacuate from the chamber at least part of the fluid introduced by the cleaning system, the drainage system comprising at least one drainage hole disposed in a bottom part of the chamber, the bottom part of the chamber having at least one drainage surface to guide fluid to the drainage hole.

7. A machine according to claim 5, further comprising a drying system that is adapted to effectuate a drying of the interior of the chamber and of the elements disposed within the chamber, the drying system comprising an inlet access in the top part of the chamber, at least one flow router situated to force an airflow into the chamber through the inlet access, and an outlet access disposed in a bottom part of the chamber through which the air flow is forced out of the chamber.

8. A method for the automatic preparation of an intravenous medication, the method comprising positioning a receptacle with a base product in a starting products area of a chamber of a machine, positioning a transfer tool that is used to prepare the intravenous medication in a transfer tools area of the chamber, positioning a container in a prepared products area of the chamber and by means of a first robot transporting the transfer tool between the transfer tools area, the starting products area and the prepared products area in order to prepare the intravenous medication, wherein the first robot carries out an intravenous medication preparation operation by picking up the transfer tool from the transfer tools area, transporting the transfer tool to the starting products area, operates on the transfer tool to cause the transfer tool to be partially or completely filled with a specific amount of the base product present in the receptacle, transporting the transfer tool with the base product to the prepared products area, and partially or completely emptying the transfer tool in the container.

9. A method according to claim 8, wherein first and second receptacles are positioned within the starting products area, each of the first and second receptacles containing a different base product, and wherein first and second transfer tools are positioned within the transfer tools area, the first transfer tool being used in conjunction with the first receptacle, the second transfer tool being used in conjunction with the second receptacle.

10. A method according to claim 8, wherein the receptacle is disposed in a substantially vertical position in the starting products area, the first robot disposing the transfer tool in a substantially vertical position and facing the receptacle to cause the total or partial filling of the transfer tool with the base product of the receptacle.

11. A method according to claim 8, wherein when the contents of the receptacle are powdered or lyophilised, the receptacle is transported from the starting products area to a reconstituting area by the first robot or by a second robot disposed within the chamber.

12. A method according to claim 11, wherein the powered or lyophilised contents are mixed with a reconstituting liquid to dissolve to produce the base product, and upon completion of the mixing the receptacle is returned back to the starting products area.

13. A method according to claim 12, wherein the first robot or second robot is adapted to shake the receptacle in the reconstituting area upon the reconstituting liquid being introduced into the receptacle.

14. A method for the automatic preparation of an intravenous medication, the method comprising positioning a receptacle with a base product in a starting products area of a chamber of a machine, positioning a transfer tool that is used to prepare the intravenous medication in a transfer tools area of the chamber, positioning a container in a prepared products area of the chamber and by means of a first robot transporting the transfer tool between the transfer tools area, the starting products area and the prepared products area in order to prepare the intravenous medication, the base product being placed into the container by the transfer tool in the prepared products area, wherein when the contents of the receptacle are powdered or lyophilised, the receptacle is transported from the starting products area to a reconstituting area by the first robot or by a second robot disposed within the chamber.

15. A method according to claim 14, wherein the first robot carries out an intravenous medication preparation operation by picking up the transfer tool from the transfer tools area, transporting the transfer tool to the starting products area, operates on the transfer tool to cause the transfer tool to be partially or completely filled with a specific amount of the base product present in the receptacle, transporting the transfer tool with the base product to the prepared products area, and partially or completely emptying the transfer tool in the container.

16. A method according to claim 15, wherein first and second receptacles are positioned within the starting products area, each of the first and second receptacles containing a different base product, and wherein first and second transfer tools are positioned within the transfer tools area, the first transfer tool being used in conjunction with the first receptacle, the second transfer tool being used in conjunction with the second receptacle.

17. A method according to claim 14, wherein the receptacle is disposed in a substantially vertical position in the starting products area, the first robot disposing the transfer tool in a substantially vertical position and facing the receptacle to cause the total or partial filling of the transfer tool with the base product of the receptacle.

18. A method according to claim 14, wherein the powered or lyophilised contents are mixed with a reconstituting liquid to dissolve to produce the base product, and upon completion of the mixing the receptacle is returned back to the starting products area.

19. A method according to claim 18, wherein the first robot or second robot is adapted to shake the receptacle in the reconstituting area upon the reconstituting liquid being introduced into the receptacle.

\* \* \* \* \*